United States Patent [19]

Murphy et al.

[11] 3,947,571

[45] Mar. 30, 1976

[54] LIPSTICK CONTAINING MICROENCAPSULATED OILS

[75] Inventors: John H. Murphy, Toms River; George Lieberman, Ocean, both of N.J.

[73] Assignee: Lanvin-Charles of the Ritz, Inc., New York, N.Y.

[22] Filed: May 6, 1974

[21] Appl. No.: 466,946

[52] U.S. Cl. ................................................. 424/64
[51] Int. Cl.² ........................................ A61K 7/025
[58] Field of Search ...................................... 424/64

[56] References Cited
UNITED STATES PATENTS

| | | | |
|---|---|---|---|
| 2,800,457 | 7/1957 | Green et al. | 252/316 |
| 3,041,289 | 7/1962 | Katchen et al. | 252/316 |
| 3,091,567 | 5/1963 | Wurzburg et al. | 426/98 X |
| 3,122,481 | 2/1964 | Wotzilka | 424/64 |
| 3,148,125 | 9/1964 | Strianse et al. | 424/64 |
| 3,279,999 | 10/1966 | Harrison et al. | 424/64 |

FOREIGN PATENTS OR APPLICATIONS

| | | | |
|---|---|---|---|
| 1,205,883 | 9/1970 | United Kingdom | 424/64 |

OTHER PUBLICATIONS

Stanford Research Institute Journal Issue No. 15, June 1967, pp. 1–5.

Anderson et al., Microencapsulation, by Graduate Students at the Harvard Business School, 1963, published by Managment Reports, pp. 1, 23, 71, 72, 74 & 77.

*Primary Examiner*—Dale R. Ore
*Attorney, Agent, or Firm*—Lawrence S. Levinson; Merle J. Smith; Stephen B. Davis

[57] ABSTRACT

Lipstick formulation comprising oils encapsulated in a water-soluble shell dispersed within an anhydrous base. The anhydrous base comprises a mixture of various waxes, oils and coloring agents. By remoistening the lips, a sustained release of the encapsulated oils is effected which imparts a shiny wet or moist look to the lips.

11 Claims, No Drawings

LIPSTICK CONTAINING MICROENCAPSULATED OILS

BACKGROUND OF THE INVENTION

Lipsticks have been used for many years to impart color to the lips. The color helps to define the mouth area while imparting cosmetic shades that are suitable with fashion trends. Such lipsticks, in general, are made of an oily vehicle comprising fat or oil stiffened to a desired consistency with waxes of various types which also serve to raise the melting point and improve the physical stability. The color is ordinarily provided by insoluble pigments such as lakes of dye finely dispersed in the oily vehicle and one or more fluorescein dye derivatives which serve to stain the lips. A solvent for the dye is also included for increasing the effectiveness of this staining on the lips.

In recent years, attempts have been made to provide a lipstick which will impart a long lasting coloring to the lips and thus lessen the need for frequent reapplication. This has been accomplished by increasing the concentration of the dye and pigment in the conventional lipstick formulation to greater than 10% by weight. However, lipsticks containing such high concentrations of dye and pigment have been found to impart a dry "cakey" look to the lips. This is particularly undesirable since current fashion trends are directed to producing a "wet" or "moist" look on the mouth. As a result, emollients, lubricants, and moisturizers are added in increased amounts to counteract the "cakey" results of the high dye and pigment containing lipstick formulations. However, these materials themselves are usually short lived on the mouth since they are mechanically removed. In addition, these materials tend to act as vehicles for the dyes and pigments causing "creeping" or "feathering" on the outer edges of the mouth. This eliminates the sharp line of definition of the mouth area for which the product was applied.

OBJECTS OF THE INVENTION

This invention is directed to a lipstick which will impart a uniform long lasting coloring to the lips. It is directed to a lipstick formulation containing low levels of pigment and dye and high levels of emollients, lubricants, and moisturizers so as to impart a "wet" or "moist" look to the lips and yet avoid the "creeping" or "feathering" effect discussed above.

SUMMARY OF THE INVENTION

These objects are achieved by including within the lipstick formulation water-soluble microcapsules containing an oil component functioning as an emollient, lubricant, or moisturizer. Thus, the lipstick contains a reservoir of ingredients which will impart a shiny "wet" or "moist" look to the lips. Sustained release of the encapsulated ingredient is effected by merely moistening the lips. It has also been found that the capsule shell material after releasing its contents forms a barrier which reduces "creeping" and minimizes mechanical removal.

DETAILED DESCRIPTION

The lipstick formulation of this invention comprises from about 2% to about 20% by weight of water-soluble microcapsules containing a core of an oily material which functions as an emollient, lubricant or moisturizer dispersed in from about 98% to about 80% by weight of an anhydrous base including waxes, oils, coloring agents, and minor amounts of other ingredients. It is preferred that the lipstick formulation comprise from about 10% to about 15% by weight of microcapsules, with about 10% being most preferred. Sufficient anhydrous base must be employed so that the formulation is rigid enough to be moldable.

Any of the waxes commonly employed in lipstick and cosmetic formulations such as candelilla, ozokerite, carnauba, synthetic cocoa butter, petrolatum USP, isopropyl lanolate, cetyl alcohol, lanolin USP, super wool wax (a lanolin alcohol fraction), glyceryl monostearate, etc., are suitable for use in this lipstick formulation. It is preferred to employ a mixture of waxes for their particular functions, for example, candelilla wax provides mold release, super wool wax provides stick strength and drag on the lips, synthetic cocoa butter provides a smooth feel, cetyl alcohol provides a velvety feel, lanolin USP makes the formulation tacky on the lips, ozokerite provides hardness, etc.

The oily components which function as emollients, lubricants, and/or moisturizers are selected from those oils normally employed in lipstick and cosmetic formulations such as oleyl alcohol, castor oil, mineral oils, liquid lanolin, sesame oil, isopropyl myristate, isopropyl palmitate, squalane, etc. It is preferred to employ a mixture of these oils for their different functions, for example, oleyl alcohol is a penetrant and color vehicle, castor oil is a color dispersing agent, mineral oil is an emollient and moisturizer, sesame oil and squalane are lubricants, etc. The oily components are preferably present in the anhydrous base as well as in the microencapsulate part of the formulation.

The dyes employed in the formulation are the U.S. Government certified colors, both Drug and Cosmetic and Food, Drug and Cosmetic grade. The pigments employed are of the inorganic grade such as iron oxides, titanium dioxides, iron sulfides, or other conventional pigments approved for cosmetic use. The dyes and pigments are employed in an amount ranging from about 1% to about 10% by weight of the formulation with about 2% to about 4% being preferred and are present in the anhydrous base part of the formulation.

The microcapsules comprise an outer shell of water-soluble material and an inner core of one or more of the oily emollients, lubricants and moisturizers set forth above, with mineral oil being the preferred core material. The shell material is continuous and self-supporting and comprises from about 50% to about 90% by weight of each microcapsule with about 70% being preferred. The core materials comprise from about 10% to about 50% by weight of each microcapsule with about 30% being preferred. The microcapsules have an average particle size less than 77 microns and preferably less than 38 microns.

The water-soluble shell material is preferably selected from food grade polymeric materials such as starches, gum arabic, gum tragacanth, dextrin, derivatives of dextrin, etc., with dextrin being the most preferred. Methods of forming microcapsules from such materials are known in the art as see for example U.S. Pat. No. 3,159,585 to Evans et al. The shell material could also be a synthetic water-soluble polymeric material such as poly(vinyl alcohol) or a water-insoluble material treated so as to become water-soluble as disclosed in U.S. Pat. No. 3,629,140 to Bayless et al.

Anhydrous natural flavor and fragrance oils such as peppermint oil, lemon oil, orange oil, etc. or synthetic flavor and fragrance oils can be included in the lipstick formulation by incorporation into either the anhydrous base or the microencapsulated oils.

Small amounts, i.e. less than 0.3% by weight of the formulation, of other ingredients such as preservatives, as for example, propyl p-hydroxybenzoate, and antioxidants, as for example butylated hydroxyanisole (BHA), can be included within the anhydrous base part of the lipstick formulation.

The lipstick when applied coats the lips with the dispersion of the anhydrous base and the oil containing water-soluble microcapsules. By remoistening the lips, a sustained release of the encapsulated oil is effected which imparts a shiny "wet" or "moist" look to the lips. The capsule shell material after releasing its contents enhances color development and allows for an easier transfer of color to the lips. The water-soluble polymer actually forms an emulsion with the oils and waxes in situ on the lips. This promotes a creamy feel on the lips and aids the water soluble colors in penetrating every pore and crevice on the lip surface. The water-soluble shell material forms a barrier which reduces "creeping" and minimizes mechanical removal of the coating. The following examples are illustrative of lipstick formulations within the scope of this invention.

EXAMPLE 1

| Ingredient | % by Weight |
|---|---|
| Candelilla wax | 13.73 |
| Oleyl alcohol | 13.22 |
| Castor oil | 13.00 |
| Super wool wax | 10.00 |
| Mineral oil | 7.50 |
| Synthetic cocoa butter | 4.00 |
| Cetyl alcohol | 5.00 |
| Liquid lanolin USP | 4.50 |
| Sesame oil | 4.50 |
| Petrolatum USP | 4.50 |
| Isopropyl lanolate | 3.00 |
| Lanolin USP | 1.50 |
| Squalane | 1.00 |
| Ozokerite | 1.00 |
| Propyl p-hydroxybenzoate | 0.10 |
| Butylated hydroxyanisole | 0.02 |
| D & C Red No. 9 | 1.66 |
| D & C Red No. 27 | 0.78 |
| Iron oxide | 0.49 |
| Fragrance oil | 0.50 |
| Encapsulate | 10.00 |

The encapsulate consists of microcapsules having an average particle size of less than 77 microns. Each microcapsule consists of 30% mineral oil and 70% water-soluble dextrin with the oil encapsulated within the dextrin shell.

The ingredients are combined according to the following procedure:

1. All of the waxes are melted in a steam-jacketed kettle with lightnin mixer agitation while maintaining the temperature at from 75 to 85°C. After the waxes are melted, the oil components except for the castor oil are added and agitation is continued.

2. The dyes and pigment are added to the castor oil in a separate kettle and heated with agitation at 70°C. Agitation is continued until a proper dispersion is achieved. The dispersion of oil and coloring agents is passed through a three-roll mill.

3. The encapsulated moisturizer is sifted through a 77 micron screen.

4. The melted waxes from step (1) and the ground coloring agent from step (2) are mixed at 75°C with lightnin agitation. After the mixing is completed the sifted encapsulated moisturizer is added. The formulation is either stored or poured directly into molds and maintained at room temparature to form the lipstick.

Alternatively, the encapsulated moisturizer can be added directly to the ground dye slurry of step (2). This mixture is passed through a three-roll mill and then added to the melted waxes from step (1) at 75°C with lightnin agitation.

EXAMPLE 2

| Ingredient | % by Weight |
|---|---|
| Candelilla wax | 14.55 |
| Oleyl alcohol | 14.20 |
| Castor oil | 13.50 |
| Super wool wax | 10.50 |
| Mineral oil | 8.00 |
| Synthetic cocoa butter | 4.25 |
| Cetyl alcohol | 5.30 |
| Liquid lanolin USP | 4.75 |
| Sesame oil | 4.75 |
| Petrolatum USP | 4.75 |
| Isopropyl lanolate | 3.10 |
| Lanolin USP | 1.60 |
| Squalane | 1.00 |
| Ozokerite | 1.00 |
| Propyl p-hydroxybenzoate | 0.10 |
| Butylated hydroxyanisole | 0.02 |
| D & C Red No. 9 | 1.86 |
| D & C Red No. 27 | 0.78 |
| Iron oxide | 0.49 |
| Fragrance oil | 0.50 |
| Encapsulate | 5.00 |

The encapsulate consists of microcapsule having an average particle size of less than 77 microns. Each microcapsule consists of 30% isopropyl myristate and 70% water soluble dextrin with the oil encapsulated within the dextrin shell.

The formulation is prepared according to the process set forth in Example 1.

EXAMPLE 3

| Ingredient | % by Weight |
|---|---|
| Candelilla wax | 12.91 |
| Oleyl alcohol | 12.14 |
| Castor oil | 12.40 |
| Super wool wax | 9.50 |
| Mineral oil | 7.00 |
| Synthetic cocoa butter | 3.75 |
| Cetyl alcohol | 4.70 |
| Liquid lanolin USP | 4.25 |
| Sesame oil | 4.25 |
| Petrolatum USP | 4.25 |
| Isopropyl lanolate | 2.90 |
| Lanolin USP | 1.40 |
| Squalane | 1.00 |
| Ozokerite | 1.00 |
| Propyl p-hydroxybenzoate | 0.10 |
| Butylated hydroxyanisole | 0.02 |
| D & C Red No. 9 | 1.56 |
| D & C Red No. 27 | 0.88 |
| Iron oxide | 0.49 |
| Fragrance oil | 0.50 |
| Encapsulate | 15.00 |

The encapsulate consists of microcapsule having an average particle size of less than 38 microns. Each microcapsule consists of 20% mineral oil and 10% isopropyl myristate and 0.1% fragrance oil encapsulated within a shell of water-soluble dextrin. The dextrin comprises 69.9% of each microcapsule.

The formulation is prepared according to the process set forth in Example 1 except that the microcapsules are sifted through a 38 micron screen in step (3).

EXAMPLE 4

| Ingredient | % by Weight |
|---|---|
| Candelilla wax | 12.15 |
| Oleyl alcohol | 11.70 |
| Castor oil | 11.60 |
| Super wool wax | 8.90 |
| Mineral oil | 6.65 |
| Synthetic cocoa butter | 3.50 |
| Cetyl alcohol | 4.40 |
| Liquid lanolin USP | 3.90 |
| Sesame oil | 3.95 |
| Petrolatum USP | 3.90 |
| Isopropyl lanolate | 2.60 |
| Lanolin USP | 1.40 |
| Squalane | 0.90 |
| Ozokerite | 0.90 |
| Propyl p-hydroxybenzoate | 0.10 |
| Butylated hydroxyanisole | 0.02 |
| D & C Red No. 9 | 1.66 |
| D & C Red No. 27 | 0.78 |
| Iron oxide | 0.49 |
| Fragrance oil | 0.50 |
| Encapsulate | 20.00 |

The encapsulate consists of microcapsule having an average particle size of less than 77 microns. Each microcapsule consists of 10% mineral oil and 90% gum arabic with the oil encapsulated within the gum arabic shell.

The formulation is prepared according to the process set forth in Example 1.

EXAMPLE 5

| Ingredient | % by Weight |
|---|---|
| Candelilla wax | 15.00 |
| Oleyl alcohol | 14.50 |
| Castor oil | 14.25 |
| Super wool wax | 11.00 |
| Mineral oil | 8.20 |
| Synthetic cocoa butter | 4.40 |
| Cetyl alcohol | 5.50 |
| Liquid lanolin USP | 4.95 |
| Sesame oil | 4.95 |
| Petrolatum USP | 4.95 |
| Isopropyl lanolate | 3.25 |
| Lanolin USP | 1.50 |
| Squalane | 1.00 |
| Ozokerite | 1.00 |
| Propyl p-hydroxybenzoate | 0.10 |
| Butylated Hydroxyanisole | 0.02 |
| D & C Red No. 9 | 1.60 |
| D & C Red No. 27 | 0.73 |
| Iron Oxide | 0.60 |
| Fragrance oil | 0.50 |
| Encapsulate | 2.00 |

The encapsulate consists of microcapsules having an average particle size of less than 77 microns. Each microcapsule consists of 50% mineral oil and 50% water-soluble gum tragacanth with the oil encapsulated within the gum tragacanth shell.

The formulation is prepared according to the process set forth in EXAMPLE 1.

What is claimed is:

1. A lipstick formulation comprising oils microencapsulated within a water-soluble shell dispersed within any anhydrous base wherein said anhydrous base comprises a mixture of waxes, oils, and coloring agents and wherein said anhydrous base is present at from about 80% to about 98% by weight of said formulation and said microcapsules are present at from about 2% to about 20% by weight of said formulation.

2. The lipstick formulation of claim 1 wherein said microcapsules consist of from about 10% to about 50% by weight of oily core materials and from about 50% to about 90% by weight of water-soluble shell material and are of an average particle size of less than 77 microns.

3. The lipstick formulation of claim 2 wherein said core includes one or more oils selected from the group consisting of oleyl alcohol, castor oil, mineral oil, liquid lanolin, sesame oil, isopropyl myristate, isopropyl palmitate, and squalane and said shell material is selected from the group consisting of starch, gum arabic, gum tragacanth, and dextrin.

4. The lipstick formulation of claim 3 wherein said microcapsule comprise from about 10% to about 15% of said formulation.

5. The lipstick formulation of claim 4 wherein said microcapsules consist of about 30% core and about 70% shell.

6. The lipstick formulation of claim 5 wherein said core material is mineral oil and said shell material is dextrin and said microcapsules comprise about 10% by weight of said lipstick formulation.

7. The lipstick formulation of claim 3 wherein said shell material is dextrin and said core material is isopropyl myristate.

8. The lipstick formulation of claim 3 wherein said core material is a mixture of mineral oil, isopropyl myristate, and fragrance oil and said shell material is dextrin.

9. The lipstick formulation of claim 1, wherein said anhydrous base comprises one or more waxes selected from the group consisting of candelilla, ozokerite, carnauba, synthetic cocoa butter, petrolatum, isopropyl lanolate, cetyl alcohol, lanolin, lanolin alcohol fraction and glyceryl monostearate and one or more oils selected from the group consisting of oleyl alcohol, castor oil, mineral oil, liquid lanolin, sesame oil, isopropyl myristate, isopropyl palmitate and squalane, and one or more D & C or F, D & C certified colors and at least one inorganic pigment.

10. The lipstick formulation of claim 9 wherein said anhydrous base includes a preservative, an antioxidant, and fragrance oil.

11. A lipstick formulation consisting essentially of the following ingredients on a percent by weight basis

| Candelilla wax | 13.73 |
|---|---|
| Oleyl alcohol | 13.22 |
| Castor oil | 13.00 |
| Lanolin alcohol fraction | 10.00 |
| Mineral oil | 7.50 |
| Synthetic cocoa butter | 4.00 |
| Cetyl alcohol | 5.00 |
| Liquid lanolin | 4.50 |
| Sesame oil | 4.50 |
| Petrolatum | 4.50 |
| Isopropyl lanolate | 3.00 |
| Lanolin | 1.50 |
| Squalane | 1.00 |
| Ozokerite | 1.00 |
| Propyl p-hydroxybenzoate | 0.10 |
| Butylated hydroxyanisole | 0.02 |
| D & C Red No. 9 | 1.66 |
| D & C Red No. 27 | .78 |
| Iron oxide | .49 |
| Fragrance oil | .50 |
| Encapsulated mineral oil | 10.00 | wherein said encapsulated mineral oil consists essentially of microcapsules having an average particle size of less than 77 microns, a water-soluble dextrin shell, and wherein said shell is present at 70% by weight and said mineral oil core is present at 30% by weight in each microcapsule.

* * * * *

UNITED STATES PATENT AND TRADEMARK OFFICE
CERTIFICATE OF CORRECTION

PATENT NO. : 3,947,571

DATED : March 30, 1976

INVENTOR(S) : John H. Murphy et al.

It is certified that error appears in the above-identified patent and that said Letters Patent are hereby corrected as shown below:

Col. 5, line 60, "any" should read --an--.

Signed and Sealed this twenty-second Day of June 1976

[SEAL]

Attest:

RUTH C. MASON
*Attesting Officer*

C. MARSHALL DANN
*Commissioner of Patents and Trademarks*